United States Patent [19]

Backhaus et al.

[11] Patent Number: 5,015,572

[45] Date of Patent: May 14, 1991

[54] APPARATUS FOR DETERMINING A PROTEOLYTIC OR ESTEROLYTIC SUBSTANCE AND METHOD FOR DETERMINING A PROTEOLYTIC OR ESTEROLYTIC SUBSTANCE USING A LAYERED APPARATUS

[75] Inventors: Jürgen Backhaus, Edingen; Dieter Mangold, Maxdorf; Wolfgang-Reinhold Knappe, Bürstadt, all of Fed. Rep. of Germany

[73] Assignee: Boehringer Mannheim GmbH, Mannheim, Fed. Rep. of Germany

[21] Appl. No.: 340,885

[22] Filed: Apr. 19, 1989

[30] Foreign Application Priority Data

Apr. 22, 1988 [DE] Fed. Rep. of Germany ....... 3813503

[51] Int. Cl.$^5$ .............................................. C12Q 1/44
[52] U.S. Cl. ....................................... 435/19; 435/23; 422/56; 422/60
[58] Field of Search ........................................... 435/19

[56] References Cited

U.S. PATENT DOCUMENTS

| 4,587,099 | 5/1986 | Rothe et al. | 422/56 |
| 4,749,648 | 6/1988 | Berger et al. | 435/19 |
| 4,814,271 | 3/1989 | Hugl et al. | 435/19 |

FOREIGN PATENT DOCUMENTS 0157361 10/1985 European Pat. Off. .

Primary Examiner—Sam Rosen
Attorney, Agent, or Firm—Felfe & Lynch

[57] ABSTRACT

Carrier-bound multicomponent detection system for the colorimetric determination of esterolytically- and/or proteolytically-active ingredients of body fluids, wherein the components of the detection system are present in different reagent layers, and where a liquid exchange between the layers is possible.

13 Claims, 1 Drawing Sheet

FIG. 1                                              PRIOR ART
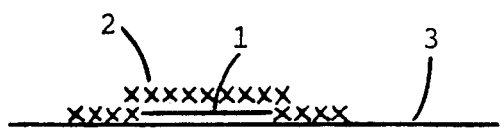
FIG. 2
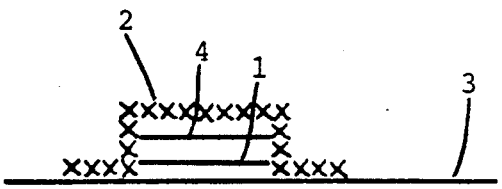

APPARATUS FOR DETERMINING A PROTEOLYTIC OR ESTEROLYTIC SUBSTANCE AND METHOD FOR DETERMINING A PROTEOLYTIC OR ESTEROLYTIC SUBSTANCE USING A LAYERED APPARATUS

BACKGROUND OF THE INVENTION

The present invention is concerned with a carrier-bound, multicomponent detection system for the colorimetric determination of esterolytically- and/or proteolytically-active ingredients of body fluids.

The detection of esterolytically- and/or proteolytically-active ingredients of body fluids is of great importance, especially in diagnosis of diseases of the kidneys and of the urogenital tract. In these cases, it is important to detect leukocytes in urine on the basis of their inherent esterolytic and/or proteolytic activity. Carrier-bound detections systems, for example in the form of test strips, have proven to be especially advantageous for this purpose because these only need to be dipped briefly into the liquid sample to be investigated and then subsequently, after removal of the strip from the sample, permit a determination of the number of leukocytes/ml of sample, for example on the basis of color formed, within a short period of time. It is thus possible to provide a clean, simple and rapid method for the detection of such ingredient materials in body fluids without complicated time- and cost-consuming manipulations having to be carried out with or on the sample for this purpose.

From the prior art, so-called multicomponent systems are taught as being advantageous detection systems for the colorimetric determination of esterolytically- and/or proteolytically-active ingredients of body fluids, for example of leukocytes, in urine. These multicomponent systems are those reagent systems which comprise several chemical substances, at least one of which is so changed by esterolytically- and/or proteolytically-active ingredients materials of body fluids that the reaction product reacts directly with another component of the detection system or reacts in a reaction sequence with several of the other components of the detection system to give a colored substance which can then be determined colorimetrically. The amount of colored substance formed is a measure of the amount of esterolytically- and/or proteolytically-active ingredients in the sample investigated.

Especially suitable for this type of detection are two-component systems in which an ester is first cleaved by the ingredient materials to be detected, followed by reaction of the resultant hydroxy compound with a further reactive substance to give a colored material. Carrier-bound multicomponent systems based upon this principle are known, for example, from U.S. Pat. Nos. 4,551,428 and 4,749,648.

These patents concern, inter alia, a carrier-bound detection system in which an ester and a diazonium salt are present on the same reagent layer. The ester reacts with a ingredient of body fluid, such as urine, which is esterolytically and/or proteolytically active. The product of the reaction is a hydroxy compound, which then reacts with the diazonium salt, forming a colored product. The joint presence of all components of the detection system on one and the same reagent layer appears to be optimal insofar as it appears to be ensured that the product resulting by reaction with the esterolytically- and/or proteolytically-active component can quickly react further to give a colored end product.

Rapid and complete detection reactions form the basis for a sensitive test. In the case of the above-mentioned detection system, the detection limit for leukocytes in urine for reading off the value after about 2 minutes is about 15 to 25 leukocytes/ul of urine. However, from the point of view of the physician, it is desirable to have available detection agents which are even more sensitive. Comparatively long waiting periods for reading off the value to be determined are undesirable.

SUMMARY OF THE INVENTION

Therefore, it is an object of the present invention to provide for medical diagnosis a carrier-bound, multicomponent detection system for the colorimetric determination of esterolytically- and/or proteolytically-active ingredients of body fluids which are more sensitive than known carrier-bound detection systems without involving the disadvantage of a comparatively long waiting time to obtain the value indicated by the detection system.

Thus, according to the present invention, the components of the detection system are present on different reagent layers situated so as to make possible liquid exchange therebetween known reagent systems which have proved to be especially advantageous contain an esterolytically- and/or proteolytically-cleavable ester and a diazonium salt. Such systems have proven efficacy, especially for the determination of leukocytes in urine. However, they can also serve for the detection of proteolytic enzymes, for example elastase, chymotrypsin or trypsin, in aqueous solutions or in body fluids, for example in whole blood, serum, liquor cerebrospinalis, pancreatic secrection or aqueous fecal extracts.

The reagent systems mentioned in the above identified patents are especially preferred in the present invention. For this purpose, at least one esterolytically- and/or proteolytically-cleavable ester and at least one diazonium salt of the type described therein are applied to separate reagent layers.

Besides the components of the detection system which participate directly in the detection reaction, such as an ester and a diazonium salt, further adjuvants can also be present. Examples of these are buffer substances, wetting agents, stabilizers and/or activators. Such adjuvants are also known, for example, from the above identified patents.

As reagent carriers, all materials which are conventionally employed for this purpose can be used, for example absorbent or swellable, porous or non-porous materials or also those which, in the case of contact with the liquid to be investigated, dissolve therein. By way of example, there may be mentioned cellulose, filter paper, synthetic fiber and glass fiber fleece, polyvinyl ester and polyamide films and also, for example, films of xanthan gum.

Carrier-bound detection agents according to the present invention contain the components of the detection system in different reagent layers. The reagents which participate directly in the detection reaction are only mixed with one another after the layers are contacted with the liquid to be investigated, whereby the reagents go at least partly into solution. The different reagent layers are separate but are arranged in such a manner that liquid exchange between them is possible. In a preferred embodiment the reagent layers containing the particular components of the detection system, for example ester and diazonium salt, are arranged above one another, more or less like a stack. For a better handling of this stack of reagent layers these can be applied, for example, to a synthetic material carrier, such as a stiff film. The fixing of the stack on to the synthetic material carrier can take place, for example, by enmeshing, by edge adhesion or by sticking one reagent carrier on to the synthetic material carrier and punctuate adhesion of the further reagent layer onto the previous one. For a better absorption of the liquid to be investigated, a non reagent carrying fleece, for example, can be placed below such a stack of reagent layers.

As materials for a reagent layer lying directly on a synthetic material carrier, synthetic material films, for example polyester or polyamide films, or absorbent materials, for example cellulose fleece are preferred. For reagent layers arranged thereover, fabrics, thin transparent porous materials, transparent films or materials which dissolve in the liquid to be investigated are especially preferred.

After contact with the liquid to be investigated, by, e.g., dipping the carrier-bound detection agents in the liquid or by the measured application of the liquid to be investigated, the components of the detection system present in the reagent layers are brought at least partly into solution, are mixed together via their dissolving into the liquid, and the detection reaction for determination of presence of esterolytically- and/or proteolytically-active ingredients takes place. Surprisingly, we have found that the carrier-bound detection agents according to the present invention are more than 100% more sensitive than the previously known agents. When a waiting time of up to 2 minutes, is used, for example, as few as 5 leukocytes/$\mu$l of sample can be determined colorimetrically. Values above 10 leukocytes/$\mu$l of sample can even be read off in as little as 1 minute after wetting the carrier-bound detection agent with the liquid sample.

The following Examples are given for the purpose of illustrating the present invention with reference to the accompanying drawing, in which:

FIG. 1 is a schematic illustration of a known detection system viewed laterally; and FIG. 2 is a schematic illustration of a detection system according to the present invention viewed laterally.

EXAMPLE 1

Sensitivity of the test for the detection of leukocytes in urine.

A) Carrier-bound detection system of the prior art according to FIG. 1 of the accompanying drawings with a single impregnation of ester and diazonium salt.

Paper Fleece 23 SL of the firm Schleicher & Schüll, Dassel, Federal Republic of Germany, was impregnated in the following manner with the adjuvants and components of the detection system:

a) Pre-impregnation with an impregnation solution which, per liter of water, contained 65 g boric acid and 21 g sodium hydroxide and which had been adjusted with 1N hydrochloric acid to pH 8.0, followed by drying the impregnated fleece.

b) Main impregnation of the buffer-impregnated fleece produced according to a) with a solution which, in one liter of ethanol, contained 0.35 g 2-methoxy-4-(N-morpholino)-benzene-diazonium tetrachlorozincate, 0.78 g 3-(N-toluene-4'-sulphonyl-L-alanyloxy)-indole, 81.3 g phosphoric acid trimorpholide and 21.7 ml decanol, followed by drying.

The so impregnated fleece was cut up into squares with the dimensions of 6×6 mm and the so produced reagent layers (1) each fixed by means of a nylon mesh (2) NY75HC (filament thickness 60 um) of the Züricher Beuteltuchfabrik AG, Zürich, Switzerland, on to a 12.6 cm long, 6 mm wide and 1 mm thick polystyrene strip (3). For this purpose, the nylon mesh was partly melted with the synthetic resin strip by heating to about 175° C.

B) Carrier-bound detection system according to FIG. 1 of the accompanying drawings with separate impregnation of the ester and diazonium salt.

A paper fleece 23 SL of the firm Schleicher & Schüll, Dassel, Federal Republic of Germany, was impregnated in the following manner with the adjuvants and components of the detection system:

a) Pre-impregnation with an impregnation solution which, in 1 liter of water, contained 65 g boric acid and 21 g sodium hydroxide which had been adjusted with 1N hydrochloric acid to pH 8.0, followed by drying.

b) Impregnation of the buffer-impregnated fleece produced according to a) with a solution which, in 1 liter of ethanol, contained 0.78 g 3-(N-toluene-4'-sulphonyl-L-alanyloxy)-indole, 81.3 g phosphoric acid trimorpholide and 21.7 ml decanol, followed by drying.

c) Impregnation of the fleece impregnated according to a) and b) with a solution which, in 1 liter of water, contained 0.37 g 2-methoxy-4-(N-morpholino)-benzene-diazonium tetrachlorozincate and 0.22 g tartaric acid, followed by drying.

Analogously to A), a carrier-bound detection system was produced according to FIG. 1 with the so impregnated paper fleece.

C) Detection system according to the present invention (FIG. 2).

I) A paper fleece 23 SL of the firm Schleicher & Schüll, Dassel, Federal Republic of Germany, was impregnated in the following way:

a) Pre-impregnation with an impregnation solution which, in 1 liter of water, contained 65 g boric acid and 21 g sodium hydroxide and adjusted to pH 8.0 with 1N hydrochloric acid, followed by drying the impregnated fleece.

b) Main impregnation of the fleece produced according to a) with a solution which, in 1 liter ethanol, contained 0.78 g 3-(N-toluene-4'-sulphonyl-L-alanyloxy)-indole, 81.3 g phosphoric acid trimorpholide and 21.7 ml decanol, followed by drying.

II) A nylon fabric NY 20 HC (filament thickness 20 um) of the firm Züricher Beuteltuchfabrik AG, Zürich, Switzerland, was impregnated with a solution which, in 1 liter of water, contained 3.78 g 2-methoxy-4-(N-morpholino)-benzenediazonium tetrachlorozincate and 2.25 g tartaric acid and subsequently dried.

The impregnated paper fleece from I) was cut into squares with the dimensions of 6×6 mm to give the reagent layer (1). The nylon fabric produced in II) was cut up into squares of the same size to give the reagent layer (4). The reagent layers (1) and (4) were fixed as a stack by means of a nylon mesh (2) NY75HC (filament thickness 60 um) of the firm Züricher Beuteltuchfabrik AG, Zürich, Switzerland, on to a 12.6 cm long, 6 mm wide and 1 mm thick polystyrene strip (3). The nylon mesh itself was fixed on to the synthetrc material strip by partial melting by heating to about 175° C. D) Leukocyte-containing solutions are produced by making up leukocyte-free urine with leukocytes isolated from blood. The following concentrations were present for the testing of the detection system: 0,5, 10, 20 and 40 leukocytes/ul of urine.

The test strips produced in A), B) and C) were dipped into the leucocyte-free and leukocyte-containing urine samples and, after 2 minutes, were read off visually or measured remission photometrically with respect to the color formation. The following results were obtained with the detection systems described in A), B) and C).

| number of leukocytes/μl of sample | color formation in the case of detection system | | | increase of the remission measured with Urotron RL-9 in remission units (Boehringer Mannheim GmbH) | | |
|---|---|---|---|---|---|---|
| | A | B | C | A | B | C |
| 0 | − | − | − | 0 | 0 | 0 |
| 5 | − | − | + | 0 | 0 | 4 |
| 10 | − | − | + | 0 | 0 | 9 |
| 20 | + | + | + | 6 | 5 | 17 |
| 40 | + | + | + | 14 | 13 | 31 |

Whereas in the case of the detection systems A) and B) (prior art) 2 minutes after sample contract, the limit of detection for leukocytes was about 20 leukocytes/μl of sample, with the detection system C) according to the present invention there were already indicated 5 leukocytes/ul of sample.

After only 1 minute, the detection system C) there detected a concentration of 10 leukocytes/μl of sample both visually and by means of remission photometry. In the case of this short time, with detection systems A) and B) the limit of detection was more than 20 leukocytes/μl of sample.

It will be understood that the specification and examples are illustrative but not limitative of the present invention and that other embodiments within the spirit and scope of the invention will suggest themselves to those skilled in the art.

We claim:

1. Apparatus useful in determining an esterolytically or proteolytically active ingredient of a body fluid, comprising a plurality of reagent containing layers, wherein said layers are positioned on a carrier in such a way as to permit liquid exchange therebetween, said plurality of reagents effecting a colorimetrically determinable signal in the presence of said esterolytically or proteolytically active ingredient, and wherein said plurality of reagent containing layers contain at least one diazonium salt comprising 2-methoxy-4(N-morpholino)-benzene-diazonium tetrachlorozincate, and at least one esterolytically or proteolytically cleavable ester comprising 3-(N-toluene-4'-sulphonyl-L-alanyloxy)-indole, wherein said diazonium salt and said ester are positioned in different layers.

2. Apparatus of claim 1, wherein said reagent containing layers are stacked on top of each other.

3. Apparatus of claim 2, wherein said stacked reagent containing layers are covered by a liquid permeable covering means.

4. Apparatus of claim 1, wherein said reagent carrying layers comprise absorbent or swellable material.

5. Apparatus of claim 1, wherein said reagent carrying layers comprise porous material.

6. Apparatus of claim 1, wherein said reagent carrying layers comprise nonporous material.

7. Apparatus of claim 1, wherein said reagent carrying layers comprise cellulose, filter paper, synthetic fibers, glass fibers, polyvinyl esters, polyamide films or xanthan gum films.

8. Method for determining an esterolytically or proteolytically active component of a body fluid comprising contacting a body fluid sample to an apparatus comprising a plurality of layers positioned on a carrier to permit a liquid exchange therebetween, one of said layers containing a diazonium salt which is 2-methoxy-4(N-morpholino)-benzene-diazonium tetrachlorozincate, and a further one of said layers containing an esterolytically or proteolytically cleavable ester which is 3-(N-toluene-4'-sulphonyl-L-alanyloxy)-indole, and determining a colorimetric signal as an indication of aid esterolytically or proteolytically active component.

9. Method of claim 8, wherein said body fluid is urine, whole blood, serum, liquor cerebrospinalis, an pancreatic secretion, or an aqueous fecal extract.

10. Method of claim 8, wherein said body fluid is urine.

11. Method of claim 8, wherein said esterolytically or proteolytically active component is a leukocyte.

12. Method of claim 8, further comprising determining said colorimetric signal in 2 minutes or less after application of said body fluid sample to said apparatus.

13. A carrier-bound multi-component detection system comprising a plurality of layers positioned on a carrier to permit a liquid exchange therebetween, said layers containing a respective plurality of reagents which effect a colorimetrically determinable signal in the presence of an esterolytically or proteolytically active ingredient of a body fluid, said layers comprising a first layer containing as reagent a diazonium salt, 2-methoxy-4(N-morpholino)-benzene-diazonium tetrachlorozincate, and a second layer containing as reagent an esterolytically or proteolytically cleavable ester, 3-(N-toluene-4'-sulphonyl-L-alanyloxy)-indole.

* * * * *